United States Patent
Fujita et al.

(10) Patent No.: US 11,457,828 B2
(45) Date of Patent: Oct. 4, 2022

(54) PULSE WAVE MEASUREMENT ELECTRODE UNIT AND PULSE WAVE MEASUREMENT DEVICE

(71) Applicants: OMRON HEALTHCARE Co., Ltd., Kyoto (JP); OMRON Corporation, Kyoto (JP)

(72) Inventors: Reiji Fujita, Kyoto (JP); Naomi Matsumura, Kyoto (JP)

(73) Assignees: OMRON CORPORATION, Kyoto (JP); OMRON HEALTHCARE CO., LTD., Kyoto (JP)

( * ) Notice: Subject to any disclaimer, the term of this patent is extended or adjusted under 35 U.S.C. 154(b) by 361 days.

(21) Appl. No.: 16/814,172

(22) Filed: Mar. 10, 2020

(65) Prior Publication Data
US 2020/0205683 A1  Jul. 2, 2020

Related U.S. Application Data

(63) Continuation of application No. PCT/JP2018/030525, filed on Aug. 17, 2018.

(30) Foreign Application Priority Data

Sep. 14, 2017  (JP) .............................. JP2017-176931

(51) Int. Cl.
*A61B 5/024* (2006.01)
*A61B 5/0245* (2006.01)
(Continued)

(52) U.S. Cl.
CPC ........ *A61B 5/02438* (2013.01); *A61B 5/0245* (2013.01); *A61B 5/681* (2013.01); *A61B 5/6843* (2013.01); *A61B 5/02125* (2013.01)

(58) Field of Classification Search
CPC ............ A61B 5/02108; A61B 5/02116; A61B 5/02125; A61B 5/02141; A61B 5/022;
(Continued)

(56) References Cited

U.S. PATENT DOCUMENTS

| 6,514,212 B1 | 2/2003 | Ide et al. |
| 2008/0021771 A1 | 1/2008 | Wu et al. |

(Continued)

FOREIGN PATENT DOCUMENTS

| CN | 1277006 | 12/2000 |
| CN | 101449138 | 6/2009 |

(Continued)

OTHER PUBLICATIONS

Decision to Grant Patent dated Mar. 23, 2021 in counterpart Japanese Application No. 2017-176931 with English translation.
(Continued)

*Primary Examiner* — Orlando Bousono
(74) *Attorney, Agent, or Firm* — Wenderoth, Lind & Ponack, L.L.P.

(57) ABSTRACT

A pulse wave measurement electrode unit (200) includes electrodes (41 to 46) including a pair of current applying electrodes and a first pair of voltage measuring electrodes; a support member (210) that supports the electrodes on a first main surface (211) that faces a body surface of a measurement subject in a case that the pulse wave measurement electrode unit is attached on the measurement subject; and a fluid bag (24) configured to expand and contract and configured to expand upon measurement to press the electrodes (41 to 46) against the body surface of the measurement subject. The support member (210) includes a length direction (L) corresponding to a circumferential direction of the device in an attached state to the measurement subject and a width direction (W) orthogonal to the length direction (L)

(Continued)

and a thickness direction. The electrodes (41 to 46) are arranged side by side in the width direction (W). Low rigidity portions are provided between adjacent electrodes, the low rigidity portions having a lower rigidity than a rigidity of portions that overlap the electrodes in the thickness direction.

6 Claims, 13 Drawing Sheets

(51) Int. Cl.
*A61B 5/00* (2006.01)
*A61B 5/021* (2006.01)

(58) Field of Classification Search
CPC ............ A61B 5/02225; A61B 5/02233; A61B 5/0225; A61B 5/0235; A61B 5/02438; A61B 5/0245; A61B 5/681; A61B 5/6824; A61B 5/6843
See application file for complete search history.

(56) References Cited

U.S. PATENT DOCUMENTS

| | | | |
|---|---|---|---|
| 2009/0151478 A1 | 6/2009 | Shimomoto et al. | |
| 2009/0247885 A1 | 10/2009 | Suzuki et al. | |
| 2010/0076328 A1 | 3/2010 | Matsumura et al. | |
| 2010/0198100 A1 | 8/2010 | Oku et al. | |
| 2017/0251934 A1* | 9/2017 | Ohno | A61B 5/0245 |
| 2017/0273580 A1* | 9/2017 | Lee | A61B 5/332 |
| 2017/0340219 A1* | 11/2017 | Sullivan | A61B 5/14551 |
| 2018/0206734 A1* | 7/2018 | Lin | A61B 5/681 |
| 2018/0353089 A1* | 12/2018 | Choi | A61B 5/02108 |
| 2019/0082980 A1* | 3/2019 | Mori | A61B 5/02125 |
| 2019/0209031 A1* | 7/2019 | Ariyama | A61B 5/02125 |

FOREIGN PATENT DOCUMENTS

| | | |
|---|---|---|
| CN | 101547634 | 9/2009 |
| CN | 106580273 | 4/2017 |
| JP | 2003169779 A | 6/2003 |
| JP | 2005-5606 | 1/2005 |
| JP | 2007-301232 A | 11/2007 |
| JP | 2008136655 A | 6/2008 |
| JP | 2008228995 A | 10/2008 |
| JP | 2008-295882 | 12/2008 |
| JP | 2009-022515 | 2/2009 |
| JP | 2009-226167 A | 10/2009 |
| JP | 2016-87 A | 1/2016 |
| WO | 2006/120754 | 11/2006 |
| WO | WO2007135895 A1 | 11/2007 |
| WO | 2008/087870 | 7/2008 |
| WO | 2008/123043 | 10/2008 |
| WO | 2017/127157 | 7/2017 |

OTHER PUBLICATIONS

International Preliminary Report on Patentability (Chapter II) of the International Preliminary Examining Authority for PCT/JP2018/030525 with search date of Jul. 8, 2019.
English translation of International Preliminary Report on Patentability (Chapter II) of the International Preliminary Examining Authority for PCT/JP2018/030525 with search date of Jul. 8, 2019.
International Search Report of the International Searching Authority for PCT/JP2018/030525 dated Oct. 9, 2018.
Translation of the International Search Report of the International Searching Authority for PCT/JP2018/030525 dated Oct. 9, 2018.
Office Action dated May 6, 2022 in corresponding Chinese Patent Application No. 201880058355.2, with English-language translation.

* cited by examiner

PULSE WAVE MEASUREMENT ELECTRODE UNIT AND PULSE WAVE MEASUREMENT DEVICE

CROSS-REFERENCE TO RELATED APPLICATIONS

This is a continuation of International Application 2017-176931, with an international filing date of Sep. 14, 2017, and International Application PCT/JP2018/030525, with an international filing date of Aug. 17, 2018, filed by applicant, the disclosure of which is hereby incorporated by reference in its entirety.

TECHNICAL FIELD

The present disclosure relates to a pulse wave measurement electrode unit and a pulse wave measurement device for measuring pulse transit time.

BACKGROUND ART

An example of a known pulse wave measurement electrode unit includes that described in JP 2008-136655 A (Patent Document 1).

The pulse wave measurement electrode unit described in Patent Document 1 includes a support member with a planar shape that includes a first main surface and a second main surface, which are front and rear surfaces in the thickness direction. The first main surface of the support member is provided with electrodes for pulse wave measurement, and the second main surface of the support member is provided with an air bag. In measuring pulse waves, the air bag expands and presses the electrode group against the surface of the wrist.

CITATION LIST

Patent Literature

Patent Document 1: JP 2008-136655 A

SUMMARY OF INVENTION

Technical Problem

In the pulse wave measurement electrode unit described in Patent Document 1, the electrodes are supported by the support member extending continuously in the direction in which the electrodes are arranged without change in thickness and the like.

Thus, when the pulse wave measurement electrode unit is attached to the measurement subject, the electrodes cannot be moved individually and at least one of the electrodes cannot come into suitable contact with an uneven body surface. In this case, the precision of detecting biological information may be decreased.

The present disclosure has been made in view of the problems described above, and an object of the present disclosure is to provide a pulse wave measurement electrode unit and a pulse wave measurement device including electrodes that can come into suitable contact with a body surface.

Solution to Problem

A pulse wave measurement electrode unit according to an embodiment of the present disclosure is configured to be attached wrapped around a measurement subject for pulse wave measurement of a measurement subject and includes:

electrodes including a pair of current applying electrodes and a first pair of voltage measuring electrodes, the electrodes coming into contact with a body surface of the measurement subject for measurement;

a support member including a first main surface that faces the body surface of the measurement subject in a case that the pulse wave measurement electrode unit is attached to the measurement subject and a second main surface, which is a surface opposite the first main surface in a thickness direction, the support member supporting the electrodes on the first main surface; and a fluid bag configured to expand and contract via the supply and discharge of fluid and configured to expand upon measurement to press the electrodes against the body surface of the measurement subject. The support member includes a length direction corresponding to a circumferential direction of the pulse wave measurement electrode unit in an attached state to the measurement subject and a width direction orthogonal to the length direction. The electrodes are arranged side by side in the width direction. Low rigidity portions are provided between adjacent electrodes of the electrodes, the low rigidity portions having a lower rigidity than a rigidity of portions overlapping the electrodes in the thickness direction.

In the pulse wave measurement electrode unit according to the embodiment of the present disclosure described above, the fluid bag may include divided bags separated from one another in the width direction and disposed between the electrodes and the first main surface of the support member. In this case, preferably, the low rigidity portions have a low rigidity due to gaps being provided between adjacent divided bags of the divided bags.

In the pulse wave measurement electrode unit according to the embodiment of the present disclosure described above, the electrodes may be provided on the first main surface and the fluid bag may be disposed on the second main surface. In this case, preferably, the low rigidity portions have a low rigidity due to notch portions or opening portions being provided in the support member at portions located between the adjacent electrodes.

In the pulse wave measurement electrode unit according to the embodiment of the present disclosure described above, the fluid bag may include notch portions or opening portions at portions corresponding to the notch portions or the opening portions of the support member.

In the pulse wave measurement electrode unit according to the embodiment of the present disclosure described above, the electrodes may include a second pair of voltage measuring electrodes. In this case, the first pair of voltage measuring electrodes and the second pair of voltage measuring electrodes may be disposed between the pair of current applying electrodes.

A pulse wave measurement device according to an embodiment of the present disclosure includes:

the pulse wave measurement electrode unit described above; and a belt member configured to support the pulse wave measurement electrode unit and wrap around a measurement site of a measurement subject.

Advantageous Effects of Invention

The present disclosure can provide a pulse wave measurement electrode unit and a pulse wave measurement device including electrodes that can come into suitable contact with a body surface.

DESCRIPTION OF EMBODIMENTS

Figure 1:
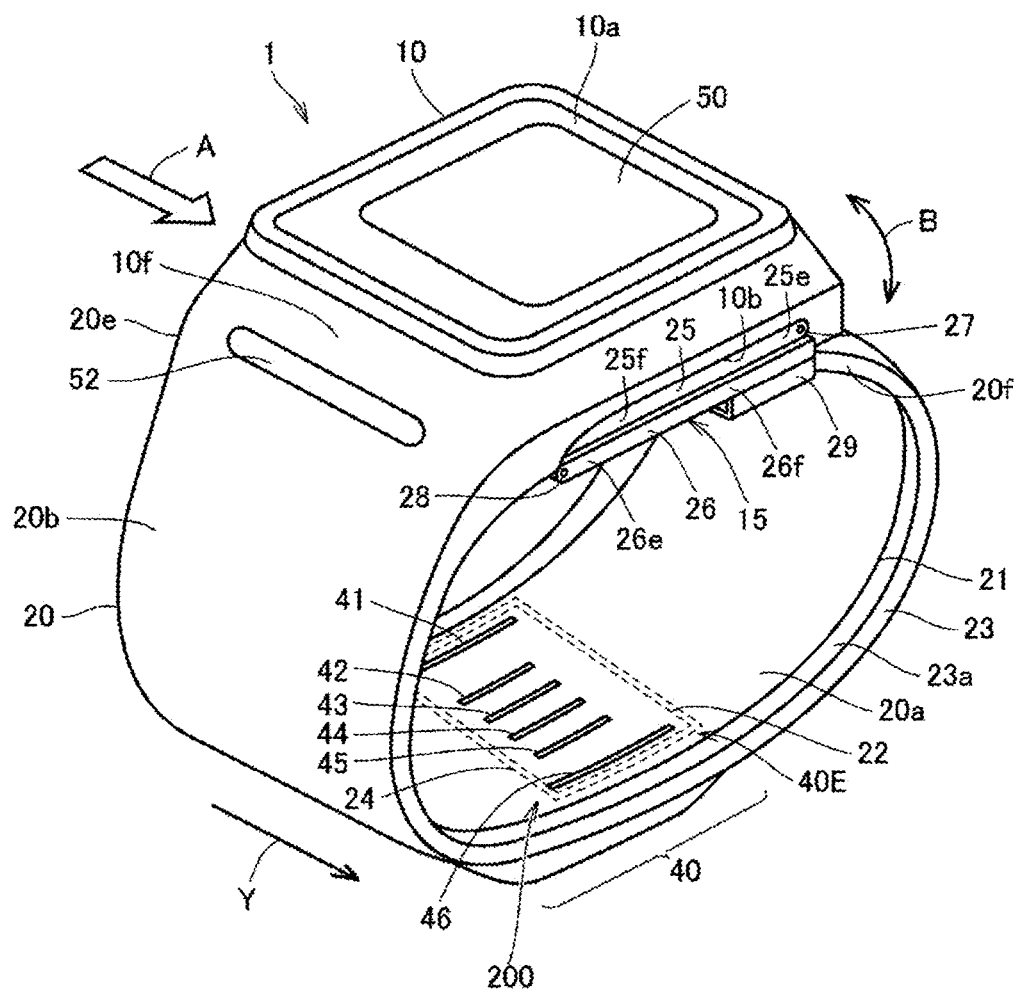
FIG. 1 is a perspective view illustrating the appearance of a blood pressure monitor according to a first embodiment.

Embodiments of the present disclosure will be described in detail below with reference to the drawings. Note that in the following embodiments, identical or common components are given the same reference signs in the drawings, and the descriptions thereof are not repeated.

First Embodiment

Figure 2:
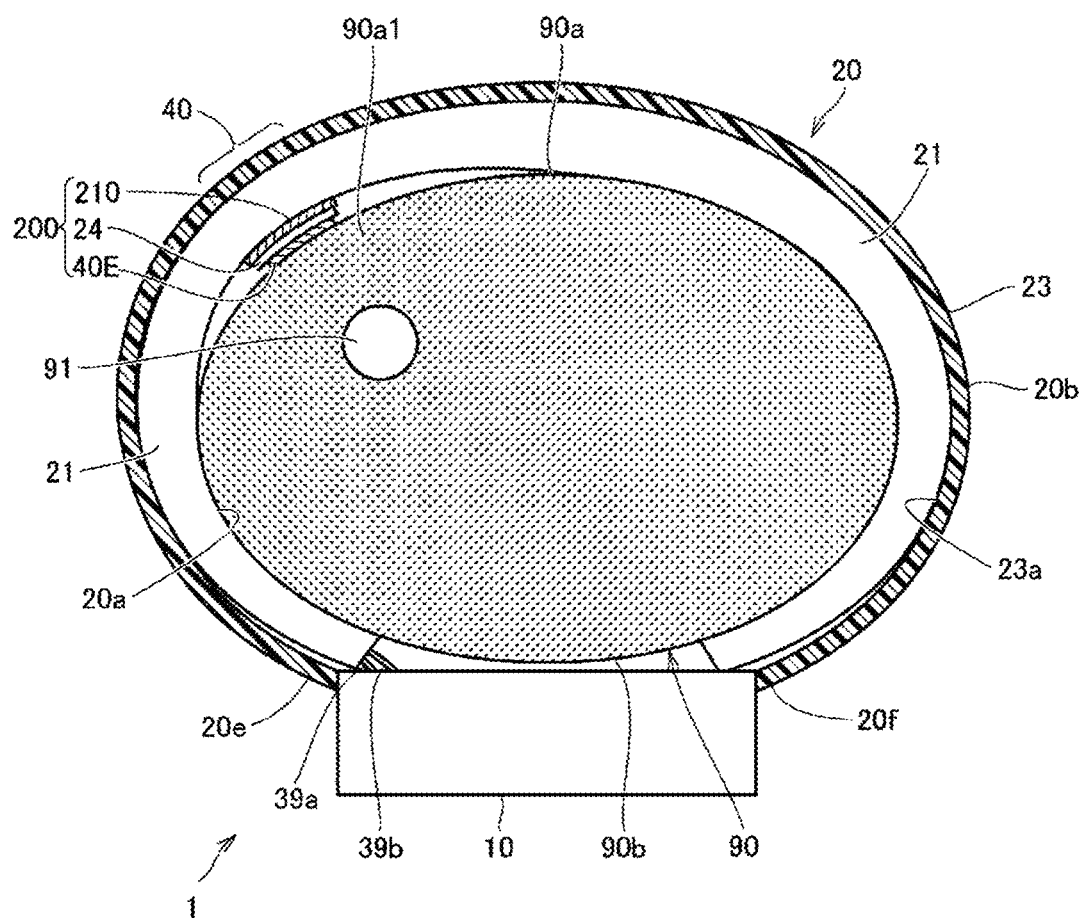
FIG. 2 is a diagram schematically illustrating the blood pressure monitor according to the first embodiment in a cross-section perpendicular to the longitudinal direction of the wrist, the blood pressure monitor being attached to the left wrist.

FIG. 1 is a perspective view illustrating the appearance of a blood pressure monitor according to a first embodiment. FIG. 2 is a diagram schematically illustrating the blood pressure monitor according to the first embodiment in a cross-section perpendicular to the longitudinal direction of the wrist, the blood pressure monitor being attached on the left wrist.

As illustrated in FIGS. 1 and 2, the blood pressure monitor 1, i.e., a pulse wave measurement device, mainly includes a belt 20 attached around a left wrist 90 of the user, a body 10 integrally attached to the belt 20, and a pulse wave measurement electrode unit 200.

The belt 20 has an elongated band-like shape allowing it to wrap around the left wrist 90 in the circumferential direction. The dimension (width dimension) of the belt 20 in a width direction Y is, for example, approximately 30 mm. The belt 20 includes a band 23 that constitutes an outer circumferential surface 20b and a compression cuff 21 attached and conforming to an inner circumferential surface 23a of the band 23. The compression cuff 21 constitutes an inner circumferential surface 20a that comes into contact with the left wrist 90. The compression cuff 21, like the belt 20, has an elongated band-like shape allowing it to wrap around the left wrist 90 in the circumferential direction.

The body 10 is integrally formed with the belt 20 at one end portion 20e in the circumferential direction via integral forming, for example. Note that the belt 20 and the body 10 may be formed separately, and the body 10 may be integrally attached to the belt 20 using an engagement member such as a hinge.

As illustrated in FIG. 2, the location where the body 10 is disposed corresponds to a back side surface (surface on the back side of the hand) 90b of the left wrist 90 when the device is worn. A radial artery 91 runs through the left wrist 90 near a palm side surface 90a (surface on the palm side of the hand).

Returning to FIG. 1, the body 10 has a thickness in the direction perpendicular to the outer circumferential surface 20b of the belt 20. The body 10 is formed compact and thin, so as to not interfere with the daily activities of the user. The body 10 has a truncated quadrangular pyramid profile protruding outward from the belt 20.

A display 50 including a display screen is provided on a top surface (surface on the far side from the target measurement site) 10a of the body 10. Also, an operation portion 52 is provided along a side surface (side surface on the left front side in FIG. 1) 10f of the body 10. The operation portion 52 is for the input of instructions from the user.

The belt 20 is provided with the pulse wave measurement electrode unit 200 on the inner circumferential surface 20a of the compression cuff 21, which constitutes the inner circumferential surface 20a of the belt 20, at a portion in the circumferential direction between a first end portion 20e and a second end portion 20f. The belt 20 supports the pulse wave measurement electrode unit 200.

The pulse wave measurement electrode unit 200 includes electrodes 41 to 46 (also collectively referred to below as "electrode group 40E"), a pressing cuff 24, i.e., a fluid bag, and a support member 210. Note that the detailed configuration of the pulse wave measurement electrode unit 200 will be described below with reference to FIG. 9.

Figure 3:
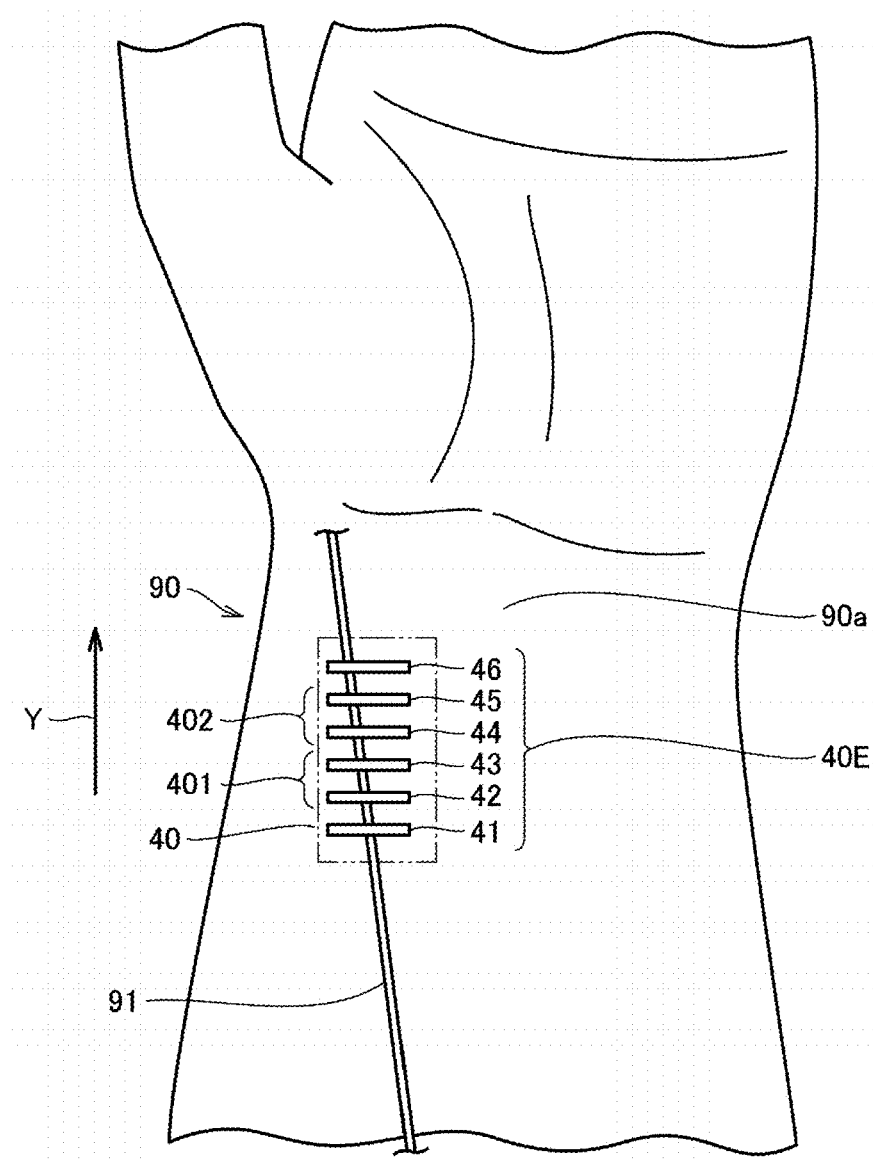
FIG. 3 is a plan view of the layout of an impedance measurement electrode that constitutes a first pulse wave sensor and a second pulse wave sensor when the blood pressure monitor according to the first embodiment is attached to the left wrist.

The pulse wave measurement electrode unit 200 includes an impedance measurement portion 40 that includes a first pulse wave sensor 401 (FIG. 3) and a second pulse wave sensor 402 (FIG. 3).

The belt 20 is provided with the six plate-like electrodes 41 to 46 at the inner circumferential surface 20a where the impedance measurement portion 40 is disposed. The electrodes 41 to 46 are separated from each other in the width direction Y of the belt 20. The location where the electrodes 41 to 46 are disposed corresponds to the radial artery 91 (see FIG. 2) of the left wrist 90 when the device is attached. The electrodes 41 to 46 each have a plate-like shape.

The pressing cuff 24 is disposed on the inner circumferential surface 20a of the compression cuff 21 that constitutes the inner circumferential surface 20a of the belt 20. The pressing cuff 24 is a fluid bag that expands and contracts in the thickness direction of the belt 20. The pressing cuff 24 is formed by welding together edge portions of two stretchable polyurethane sheets layered in the thickness direction. The pressing cuff 24 is put in a pressurized state when fluid is supplied and in a non-pressurized state when fluid is discharged.

As illustrated in FIG. 1, a bottom surface (surface on the near side to the target measurement site) 10b of the body 10 and the end portion 20f of the belt 20 are connected via a tri-fold buckle 15. The buckle 15 includes a first plate-like member 25 disposed on the outer circumference side and a second plate-like member 26 disposed on the inner circumference side.

A first end portion 25e of the first plate-like member 25 is attached in a freely rotatable manner to the body 10 via a connecting rod 27 that extends in the width direction Y. A second end portion 25f of the first plate-like member 25 is attached in a freely rotatable manner to a first end portion 26e of the second plate-like member 26 via a connecting rod 28 that extends in the width direction Y. A second end portion 26f of the second plate-like member 26 is fixed at a position near the end portion 20f of the belt 20 via a fixing portion 29.

Note that the attachment position of the fixing portion 29 in the circumferential direction of the belt 20 is set in advance in accordance with the circumference length of the left wrist 90 of the user. Thus, the blood pressure monitor 1 (belt 20) is formed in an overall substantially annular shape, and the buckle 15 can open and close in an arrow B direction to separate and bring together the bottom surface 10b of the body 10 and the end portion 20f of the belt 20.

When the blood pressure monitor 1 is worn on the left wrist 90, the buckle 15 is opened to increase the annular diameter of the belt 20 and the user puts their left hand through the belt 20 in the arrow A direction illustrated in FIG. 1. Then, as illustrated in FIG. 2, the user adjusts the angular position of the belt 20 around the left wrist 90 and positions the impedance measurement portion 40 of the belt 20 above the radial artery 91 running through the left wrist 90. This bring the electrode group 40E of the impedance measurement portion 40 into contact with a portion 90a1 of the palm side surface 90a of the left wrist 90 corresponding to the radial artery 91. In this way, the user wears the blood pressure monitor 1 (belt 20) on the left wrist 90.

As illustrated in FIG. 2, the band 23 has flexibility in the thickness direction and is made of a plastic material that is substantially non-stretchable in the circumferential direction (longitudinal direction). The compression cuff 21 is formed by, for example, welding together edge portions of two stretchable polyurethane sheets layered in the thickness direction. The electrode group 40E of the impedance measurement portion 40 is disposed at a position on the inner circumferential surface 20a of the belt 20 corresponding to the radial artery 91 of the left wrist 90.

FIG. 3 is a plan view of the layout of an impedance measurement electrode that constitutes a first pulse wave sensor and a second pulse wave sensor when the blood pressure monitor according to the first embodiment is attached on the left wrist.

As illustrated in FIG. 3, when the device is worn, the electrodes of the electrode group 40E of the impedance measurement portion 40 are arranged side by side in the longitudinal direction of the wrist (the width direction Y of the belt 20) following the radial artery 91 of the left wrist 90. The electrode group 40E includes a current-conducting current electrode pair 41, 46 (pair of current applying electrodes) disposed on either side in the width direction Y, a first detection electrode pair 42, 43 (pair of voltage measuring electrodes) that constitutes a first pulse wave sensor 401, and a second detection electrode pair 44, 45 (pair of voltage measuring electrodes) that constitutes a second pulse wave sensor 402.

The first pulse wave sensor 401 and the second pulse wave sensor 402 are disposed between the current electrode pair 41, 46. The first detection electrode pair 42, 43 and the second detection electrode pair 44, 45 are both electrodes for voltage measurement.

The second detection electrode pair 44, 45 is disposed downstream of the first detection electrode pair 42, 43 in the blood flow direction of the radial artery 91. A distance D (see FIG. 5A) in the width direction Y between a central point between the first detection electrode pair 42, 43 and a central point between the second detection electrode pair 44, 45 is approximately 20 mm, for example. The distance D corresponds to the actual interval between the first pulse wave sensor 401 and the second pulse wave sensor 402. Furthermore, the interval in the width direction Y between the first detection electrode pair 42, 43 is approximately 2 mm, and the interval in the width direction Y between the second detection electrode pair 44, 45 is approximately 2 mm, for example.

The electrode group 40E can have a flat configuration. Thus, the belt 20 of the blood pressure monitor 1 can have an overall thin configuration. Also, the electrode group 40E can have a flexible configuration. Thus, the electrode group 40E does not interfere with the compression of the left wrist 90 by the compression cuff 21, preventing a decrease in the precision of the blood pressure measurement performed via the oscillometric method described below.

Figure 4:
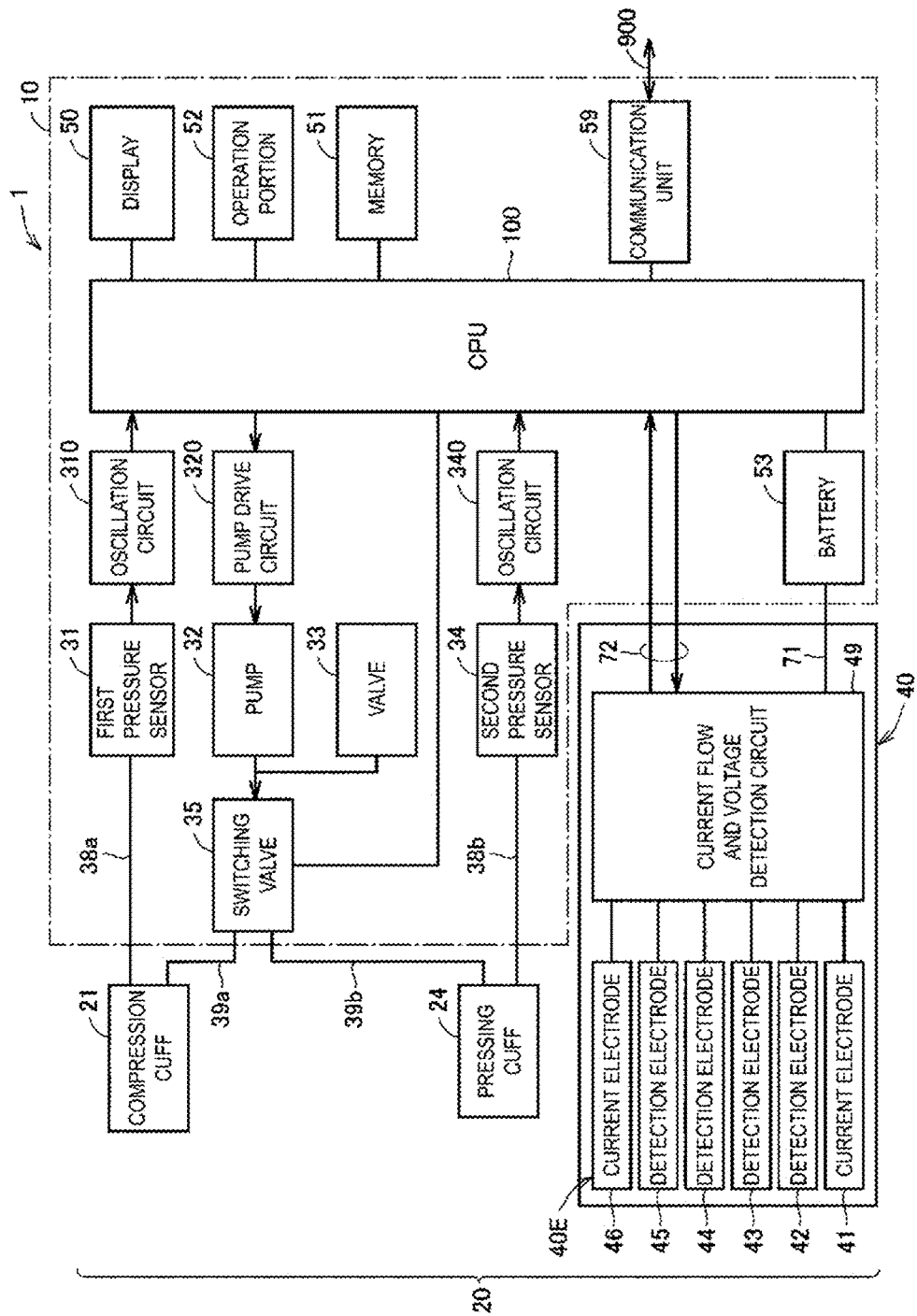
FIG. 4 is a block diagram illustrating the control configuration of the blood pressure monitor according to the first embodiment.

FIG. 4 is a block diagram illustrating the control configuration of the blood pressure monitor according to the first embodiment. Referring to FIG. 4, the control configuration of the blood pressure monitor 1 will be described.

As illustrated in FIG. 4, the display 50 and the operation portion 52 described above and a CPU 100, i.e., control unit, a memory 51, i.e., a storage unit, and a communication unit 59 are disposed in the body 10 of the blood pressure monitor 1. Also, a first pressure sensor 31, a pump 32, i.e., a fluid supply source, a valve 33, and a second pressure sensor 34 are disposed in the body 10. Also, an oscillation circuit 310 and an oscillation circuit 340 that convert the output of the first pressure sensor 31 and the second pressure sensor 34, respectively, into a frequency and a pump drive circuit 320 that drives the pump 32 are disposed in the body 10. Also, the electrode group 40E described above and a current flow and voltage detection circuit 49 are disposed in the impedance measurement portion 40. Also, a switching valve 35 for switching the connection destination of the pump 32 and the valve 33 between the compression cuff 21 and the pressing cuff 24 is provided.

The display 50 includes an organic EL display, for example. The display 50 displays information relating to blood pressure measurement such as blood pressure measurement results and other information in accordance with a control signal from the CPU 100. Note that the display 50 is not limited to being an organic EL display and may be another type of display such as a liquid crystal display.

The operation portion 52 includes, for example, a push type switch and inputs to the CPU 100 an operation signal in response to an instruction from the user to start or stop blood pressure measurement. Note that the operation portion 52 is not limited to being a push type switch and may be, for example, a pressure sensitive type (resistance type) or a proximity type (capacitance type) touch panel type switch. Also, a microphone (not illustrated) may be provided for input of a start blood pressure measurement instruction from the user via sound.

The memory 51 non-transitorily stores data of a program for controlling the blood pressure monitor 1, data used to control the blood pressure monitor 1, settings data for setting various functions of the blood pressure monitor 1, data of measurement results of blood pressure values, and the like. Also, the memory 51 is used as working memory and the like for executing a program.

The CPU 100 executes various functions as a control unit in accordance with a program for controlling the blood pressure monitor 1 stored in the memory 51. For example, in the case where blood pressure measurement is executed via the oscillometric method, the CPU 100 drives the pump 32 (and the valve 33) in accordance with a blood pressure measurement start instruction from the operation portion 52 on the basis of a signal from the first pressure sensor 31. Also, the CPU 100 calculates the blood pressure value on the basis of a signal from the first pressure sensor 31, for example.

In the case where blood pressure measurement (estimation) based on pulse transit time is executed, the CPU 100 drives the valve 33 so that air inside the compression cuff 21 is discharged in accordance with a blood pressure measurement start instruction from the operation portion 52. Also, the CPU 100 drives the switching valve 35 and switches the connection destination of the pump 32 (and the valve 33) to the pressing cuff 24. Furthermore, the CPU 100 calculates the blood pressure value on the basis of a signal from the second pressure sensor 34.

The communication unit 59 is controlled by the CPU 100, sends predetermined information to an external device via a network 900 and receives information from an external device via the network 900, and relays the information to the CPU 100. The communication via the network 900 may be wireless or wired. In the present embodiment, the network 900 is the Internet (trademark), but it is not limited thereto. The network 900 may be another network such as an intra-hospital LAN or a one-to-one communication using a USB cable or the like. The communication unit 59 may include a USB connector.

The pump 32 and the valve 33 are connected to the compression cuff 21 and the pressing cuff 24 via the switching valve 35 and air lines 39*a*, 39*b*. Also, the first pressure sensor 31 is connected to the compression cuff 21 via an air line 38*a*. The first pressure sensor 31 detects the pressure in the compression cuff 21. The second pressure sensor 34 is connected to the pressing cuff 24 via an air line 38*b*. The second pressure sensor 34 detects the pressure in the pressing cuff 24.

The switching valve 35 is driven in accordance with a control signal from the CPU 100 and switches the connection destination of the pump 32 and the valve 33 between the compression cuff 21 and the pressing cuff 24. The pump 32 includes a piezoelectric pump, for example.

In the case where the connection destination of the pump 32 and the valve 33 is switched to the compression cuff 21 by the switching valve 35, the pump 32 supplies air, i.e., pressurization fluid, into the compression cuff 21 via the air line 39*a*. This pressurizes the inside of the compression cuff 21.

In the case where the connection destination of the pump 32 and the valve 33 is switched to the pressing cuff 24 by the switching valve 35, the pump 32 supplies air, i.e., pressurization fluid, into the pressing cuff 24 via the air line 39*b*. This pressurizes the inside of the pressing cuff 24.

The pump 32 is provided with the valve 33, and the valve 33 is configured to be controlled to be open and closed in accordance with the pump 32 being on and off.

When the connection destination of the pump 32 and the valve 33 is switched to the compression cuff 21 via the switching valve 35 and the pump 32 is turned on, the valve 33 closes. This allows air to be supplied inside the compression cuff 21. When the pump 32 is turned off, the valve 33 opens. This allows the air inside the compression cuff 21 to discharge out into the atmosphere via the air line 39*a*.

When the connection destination of the pump 32 and the valve 33 is switched to the pressing cuff 24 via the switching valve 35 and the pump 32 is turned on, the valve 33 closes. This allows air to be supplied inside the pressing cuff 24. When the pump 32 is turned off, the valve 33 opens. This allows the air inside the pressing cuff 24 to discharge out into the atmosphere via the air line 39*b*.

Note that, the valve 33 functions as a check valve, preventing the discharged air from flowing in reverse. The pump drive circuit 320 drives the pump 32 on the basis of a control signal from the CPU 100.

As the first pressure sensor 31, a piezoresistive pressure sensor can be used, for example. The first pressure sensor 31 is connected to the pump 32, the valve 33, and the compression cuff 21 via an air line 38*a*. The first pressure sensor 31 detects the pressure of the belt 20 (compression cuff 21) via the air line 38*a* and outputs a time series signal. Note that the pressure is detected using atmospheric pressure as a reference (zero).

The oscillation circuit 310 produces an oscillating electrical signal on the basis of the change in electric resistance of the first pressure sensor 31 due to the piezoresistive effect. In this way, the oscillation circuit 310 outputs to the CPU 100 a frequency signal having a frequency corresponding to the electrical signal value of the first pressure sensor 31. For example, the output of the first pressure sensor 31 is used to control the pressure of the compression cuff 21 and to calculate blood pressure values (including for systolic blood pressure and for diastolic blood pressure) via the oscillometric method.

In the case where blood pressure is measured in accordance with a typical oscillometric method, generally, the following occurs. Prior to measurement, the cuff is wrapped around the target measurement site (arm or the like) of the subject. In the measurement, the CPU 100 controls the pump 32 and the valve 33 to increase the cuff pressure above the systolic blood pressure, and then gradually decreases the cuff pressure. In the reducing pressure process, the cuff pressure is detected by the pressure sensor, and the variation of arterial volume generated in the artery at the target measurement site is determined to be a pulse wave signal. The systolic blood pressure and diastolic blood pressure are calculated on the basis of the change in amplitude of the pulse wave signal corresponding to the change in the cuff pressure at the time (mainly, a rising edge and a falling edge).

As the second pressure sensor 34, a piezoresistive pressure sensor can be used, for example. The second pressure sensor 34 is connected to the pump 32, the valve 33, and the pressing cuff 24 via an air line 38b. The second pressure sensor 34 detects the pressure of the pressing cuff 24 via the air line 38b and outputs a time series signal. Note that the pressure is detected using atmospheric pressure as a reference (zero).

The oscillation circuit 340 produces an oscillating electrical signal on the basis of the change in electric resistance in the second pressure sensor 34 due to the piezoresistive effect. In this way, the oscillation circuit 340 outputs to the CPU 100 a frequency signal having a frequency corresponding to the electrical signal value of the second pressure sensor 34. For example, the output of the second pressure sensor 34 is used to control the pressure of the pressing cuff 24 and to calculate the blood pressure on the basis of pulse transit time. When the pressure of the pressing cuff 24 is controlled to measure the blood pressure on the basis of pulse transit time, the CPU 100 controls the pump 32 and the valve 33 and increases and reduces the pressure, i.e., cuff pressure, in accordance with various conditions.

A battery 53 supplies power to the components disposed in the body 10 including, in the present embodiment, the CPU 100, the first pressure sensor 31, the pump 32, the valve 33, the display 50, the memory 51, the communication unit 59, the oscillation circuit 310, and the pump drive circuit 320. Also, the battery 53 supplies power to the current flow and voltage detection circuit 49 of the impedance measurement portion 40 via a wire 71. The wire 71 is disposed together with a wire 72 for signals between the band 23 and the compression cuff 21 of the belt 20 and extends in the circumferential direction of the belt 20 between the body 10 and the impedance measurement portion 40.

Figure 5A:
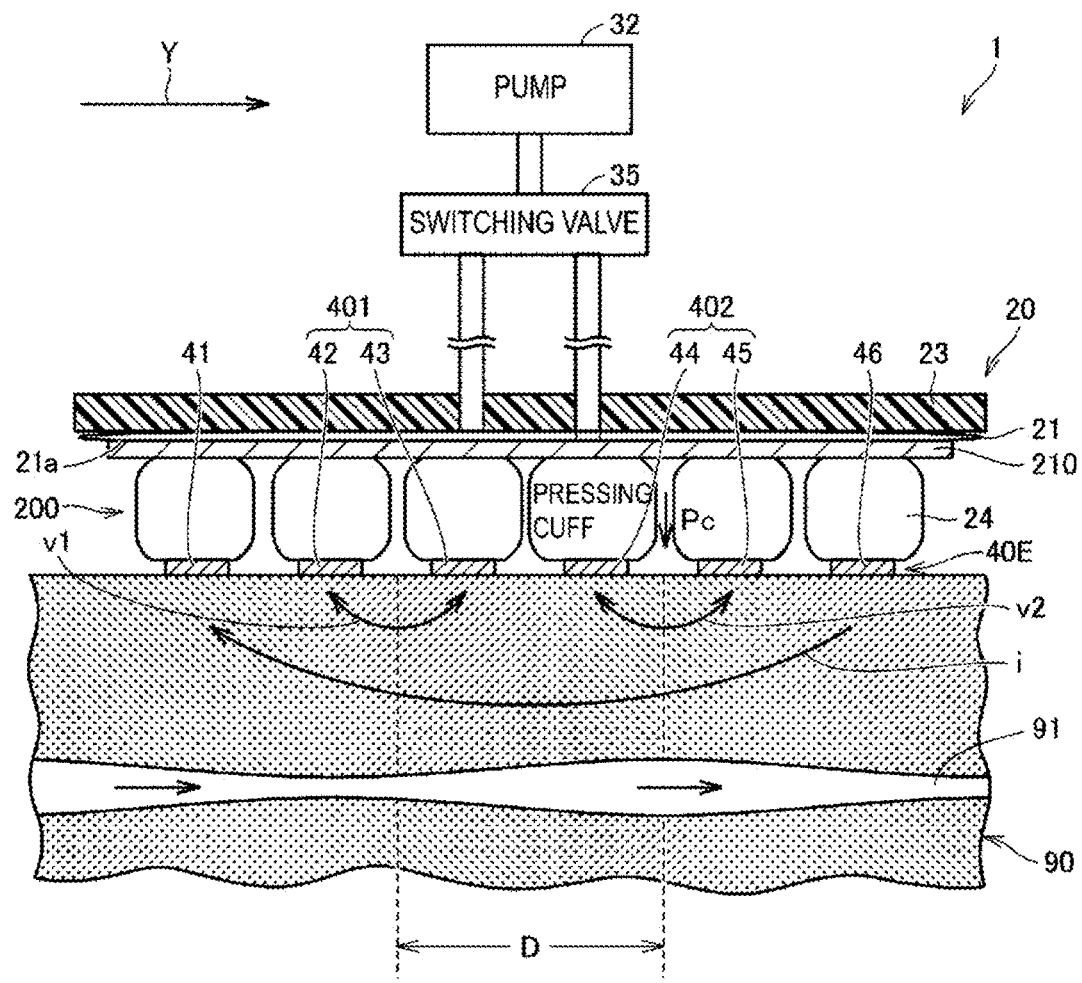
FIG. 5A is a diagram schematically illustrating the blood pressure monitor according to the first embodiment in an attached state on the left wrist in a cross-section along the longitudinal direction of the wrist as it is when blood pressure measurement is performed on the basis of pulse transit time.
Figure 5B:
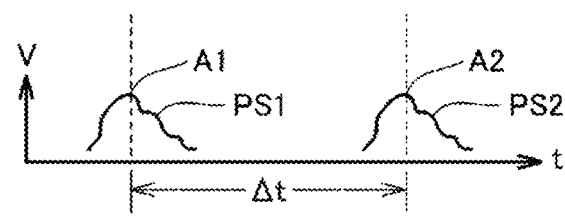
FIG. 5B is a diagram illustrating a first pulse wave signal waveform and a second pulse wave signal waveform output by a first pulse wave sensor and a second pulse wave sensor respectively in blood pressure measurement performed in the state illustrated in FIG. 5A.

FIG. 5A is a diagram schematically illustrating the blood pressure monitor according to the first embodiment in an attached state on the left wrist in a cross-section along the longitudinal direction of the wrist as it is when blood pressure measurement is performed on the basis of pulse transit time. FIG. 5B is a diagram illustrating a first pulse wave signal waveform and a second pulse wave signal waveform output by the first pulse wave sensor and the second pulse wave sensor respectively in blood pressure measurement performed in the state illustrated in FIG. 5A.

The current flow and voltage detection circuit 49 of the impedance measurement portion 40 is controlled by the CPU 100. As illustrated in FIG. 5A, when the device is operating, the CPU 100 runs a high frequency constant current i between the current electrode pair 41, 46 disposed on either side in the longitudinal direction of the wrist (the width direction Y of the belt 20). For example, the high frequency constant current i is a current with a frequency of 50 kHz and a current value of 1 mA. With the high frequency constant current i running through the current electrode pair 41, 46, the current flow and voltage detection circuit 49 detects a voltage signal v1 between the first detection electrode pair 42, 43 of the first pulse wave sensor 401 and a voltage signal v2 between the second detection electrode pair 44, 45 of the second pulse wave sensor 402.

The voltage signals v1, v2 represent a change in electrical impedance caused by a pulse wave of the blood flow of the radial artery 91 at the portions corresponding to the where the first pulse wave sensor 401 and the second pulse wave sensor 402 are located on the palm side surface 90a of the left wrist 90 (impedance method). The current flow and voltage detection circuit 49 rectifies, amplifies, and filters the voltage signals v1, v2 and outputs a first pulse wave signal PS1 and a second pulse wave signal PS2 having a mountain-shaped waveform as illustrated in FIG. 5B as time series. In the present embodiment, the voltage signals v1, v2 are approximately 1 mV. Also, peaks A1, A2 of the first pulse wave signal PS1 and the second pulse wave signal PS2 are 1 V, for example.

Note that in the case where the pulse wave velocity (PWV) of the blood flow of the radial artery 91 ranges from 100 cm/s to 2000 cm/s, a time difference Δt between the first pulse wave signal PS1 and the second pulse wave signal PS2 ranges from 1.0 ms to 2.0 ms, where an actual interval D1 between the first pulse wave sensor 401 and the second pulse wave sensor 402 is 20 mm.

As illustrated in FIG. 5A, the pressing cuff 24 is in a pressurized state, and the compression cuff 21 is in a non-pressurized state with air being discharged from inside the compression cuff 21. The pressing cuff 24 is disposed, with respect to the thickness direction of the belt 20, overlapping the first pulse wave sensor 401, the second pulse wave sensor 402, and the current electrode pair 41, 46.

As such, when the pressing cuff 24 is pressurized by the pump 32, the first pulse wave sensor 401, the second pulse wave sensor 402, and the current electrode pair 41, 46 are pressed against the palm side surface 90a of the left wrist 90.

Note that the pressing force against the palm side surface 90a of the left wrist 90 of each of the current electrode pair 41, 46, the first pulse wave sensor 401, and the second pulse wave sensor 402 can be set appropriately.

In the present embodiment, using the pressing cuff 24 allows the pump 32 and the valve 33 to be used together with the compression cuff 21 and allows the configuration to be simplified. Also, the first pulse wave sensor 401, the second pulse wave sensor 402, and the current electrode pair 41, 46 can be suitably brought into contact with the body surface in the manner described below. This allows the pressing force against the target measurement site to be substantially even. As a result, blood pressure measurement based on pulse transit time can be performed with high precision.

Figure 6:
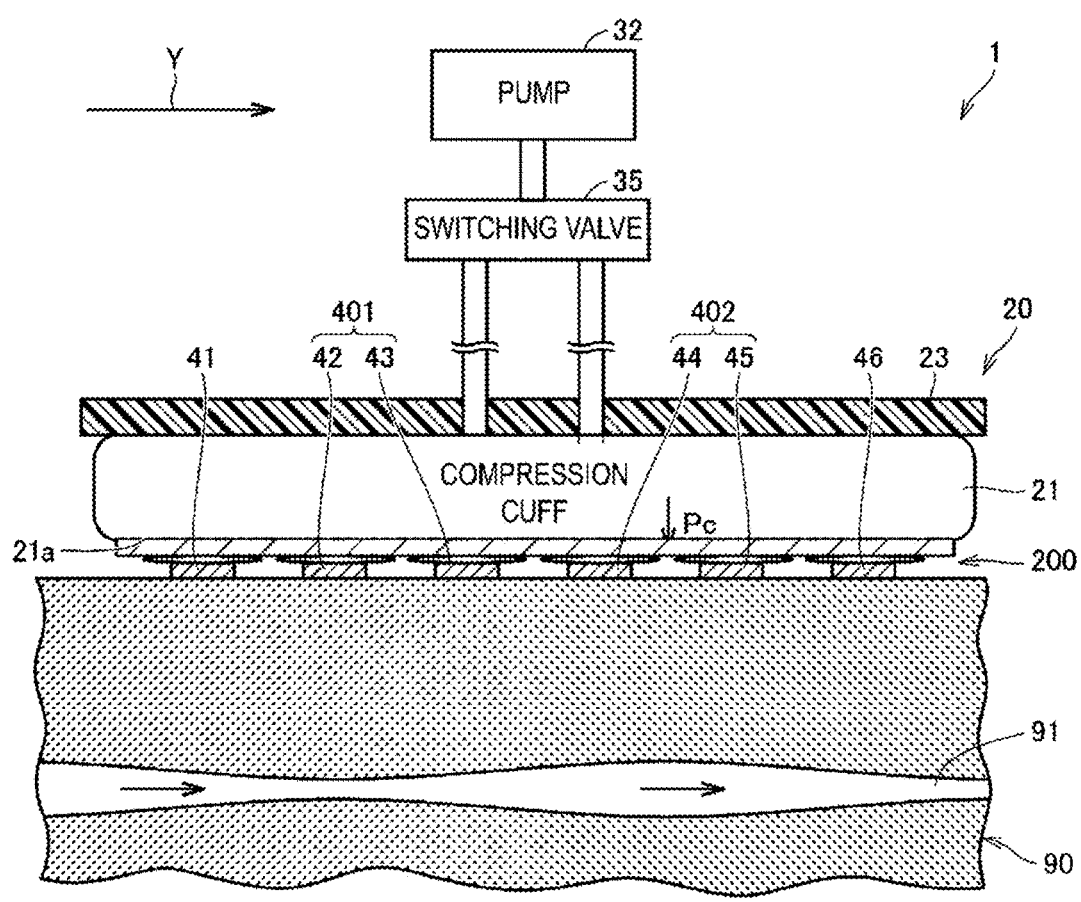
FIG. 6 is a diagram schematically illustrating the blood pressure monitor according to the first embodiment in an attached state on the left wrist in a cross-section along the longitudinal direction of the wrist as it is when blood pressure measurement is performed via the oscillometric method.

FIG. 6 is a diagram schematically illustrating the blood pressure monitor according to the first embodiment in an attached state on the left wrist in a cross-section along the longitudinal direction of the wrist as it is when blood pressure measurement is performed via the oscillometric method. In this case, the pressing cuff 24 is in a non-pressurized state with air being discharged from inside the pressing cuff 24, and the compression cuff 21 is in a state of being supplied with air. The compression cuff 21 extends in the circumferential direction of the left wrist 90 and compresses the left wrist 90 uniformly with respect to the circumferential direction of the left wrist 90 when pressurized by the pump 32. Between the inner circumferential surface 21a of the compression cuff 21 and the left wrist 90, only the flat pulse wave measurement electrode unit 200 is present. Thus, the blood vessel can be sufficiently closed without other members hindering the compression by the compression cuff 21. Thus, blood pressure measurement via the oscillometric method can be performed with high precision.

Figure 7:
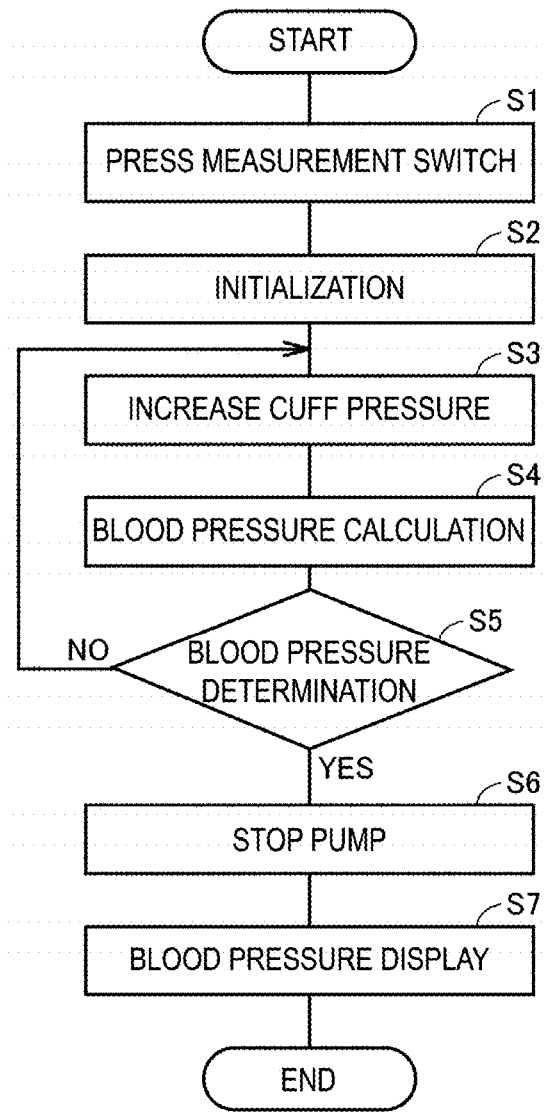
FIG. 7 is a diagram illustrating the operation flow of blood pressure measurement via the oscillometric method using the blood pressure monitor according to the first embodiment.

FIG. 7 is a diagram illustrating the operation flow of blood pressure measurement via the oscillometric method using the blood pressure monitor according to the first embodiment.

In the case where blood pressure measurement is performed via the oscillometric method, when the user sends an instruction for blood pressure measurement via the oscillometric method via the push type switch, i.e., the operation portion 52, provided on the body 10 (step S1), the CPU 100 starts operations and initializes a memory region for processing (step S2). The CPU 100 turns off the pump 32 via the pump drive circuit 320, opens the valve 33, and discharges the air in the compression cuff 21. Next, the output value of the first pressure sensor 31 at this time is set as a value corresponding to atmospheric pressure (adjusted to 0 mmHg).

Next, the CPU 100 closes the valve 33 and then drives the pump 32 via the pump drive circuit 320 to supply air to the compression cuff 21. This causes the compression cuff 21 to expand and the cuff pressure to gradually increase (step S3).

In the process of pressurizing, to calculate the blood pressure value, the CPU 100 monitors the cuff pressure via the first pressure sensor 31 and obtains, as a pulse wave signal, a variable component of the arterial volume generated in the radial artery 91 of the left wrist 90, i.e., the target measurement site.

Next, the CPU 100 functions as a second blood pressure calculation unit and attempts to calculate blood pressure values (of systolic blood pressure and diastolic blood pressure) on the basis of the obtained pulse wave signal at this point in time via the oscillometric method using a known algorithm.

At this point, if the blood pressure value cannot be calculated due to a lack of data (step S5: NO), unless the cuff pressure reaches an upper pressure limit, the processing of steps S3 to S5 are repeated. Note that the upper pressure limit is set in advance and may be 300 mmHg, for example.

If the blood pressure values can be calculated (step S5: YES), the CPU 100 stops the pump 32 via the pump drive circuit 320, opens the valve 33, and discharges the air in the compression cuff 21 (step S6). Lastly, the CPU 100 displays the blood pressure value measurement results on the display 50 and stores them in the memory 51 (step S7).

Note that the calculation of the blood pressure values is not limited being performed in the pressurizing process as described above and may be performed in the depressurizing process.

Figure 8:
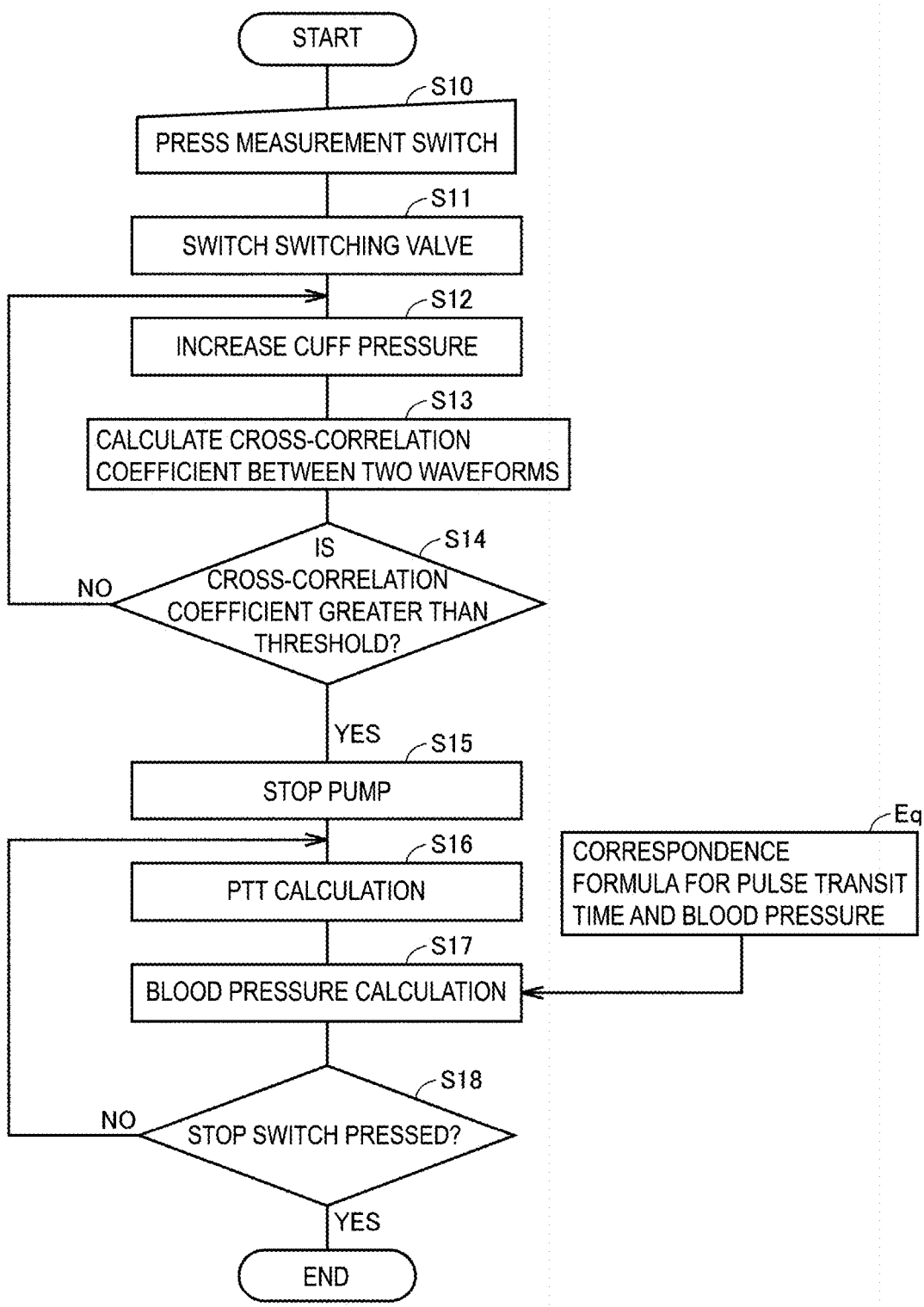
FIG. 8 is a diagram illustrating the operation flow of blood pressure measurement (estimation) based on pulse transit time (PTT) using the blood pressure monitor according to the first embodiment to obtain pulse transit time.

FIG. 8 is a diagram illustrating the operation flow of blood pressure measurement (estimation) based on pulse transit time (PTT) using the blood pressure monitor according to the first embodiment to obtain pulse transit time.

As illustrated in FIG. 8, in the case where blood pressure measurement (estimation) is performed on the basis of pulse transit time, when the user sends an instruction for blood pressure measurement based on PTT via the push type switch, i.e., the operation portion 52, provided on the body 10 (step S10), the CPU 100 drives the switching valve 35 and switches the connection destination of the pump 32 and the valve 33 to the pressing cuff 24 (step S11). Next, the CPU 100 closes the valve 33 and drives the pump 32 via the pump drive circuit 320 to supply air to the pressing cuff 24. This causes the pressing cuff 24 to expand and the cuff pressure to gradually increase (step S12). For example, the cuff pressure is continuously increased at a constant speed by 5 mmHg/s. Note that the cuff pressure may be increased in steps to secure enough time to calculate a cross-correlation coefficient r described below.

In the pressurizing process, the CPU 100 functions a cross-correlation coefficient calculation unit, obtains the first pulse wave signal PS1 and the second pulse wave signal PS2 output as time series by the first pulse wave sensor 401 and the second pulse wave sensor 402, and calculates in real time the cross-correlation coefficient r between the waveforms of the first pulse wave signal PS1 and the second pulse wave signal PS2 (step S13).

Also, the CPU 100 functions as a pressing force setting unit and determines whether the calculated cross-correlation coefficient r is greater than a preset threshold Th (step S14). For example, the threshold Th is 0.99.

If the cross-correlation coefficient r is equal to or less than the threshold Th (step S14: NO), the processing of steps S12 to S14 is repeated until the cross-correlation coefficient r is greater than the threshold Th. If the cross-correlation coefficient r is greater than the threshold Th (step S14: YES), the CPU 100 stops the pump 32 (step S15) and sets the cuff pressure as the current value, i.e., the value at the point in time when the cross-correlation coefficient r became greater than the threshold Th.

In this state, the CPU 100 obtains the time difference Δt (see FIG. 5B) between the first pulse wave signal PS1 and the second pulse wave signal PS2 as a pulse transit time PTT (step S16). Specifically, the time difference Δt between the peak A1 of the first pulse wave signal PS1 and the peak A2 of the second pulse wave signal PS2 in FIG. 5B is determined to be the pulse transit time.

Obtaining the pulse transit time in this way can increase the measurement precision of the pulse transit time. Also, by setting the cuff pressure as the value at the point in time when the cross-correlation coefficient r became greater than the threshold Th, the pulse transit time can be obtained without needlessly increasing cuff pressure. This can reduce the physical burden on the user.

Next, the CPU 100 functions as a first blood pressure calculation unit and calculates (estimates) blood pressure on the basis of the pulse transit time obtained in step S16 using a preset correspondence formula for pulse transit time and blood pressure (step S17).

By blood pressure being calculated (estimated) in this way, the measurement precision of pulse transit time described above can be increased and blood pressure measurement precision can be increased. Note that the blood pressure value measurement results are displayed on the display 50 and stored in the memory 51.

In the present embodiment, in step S18, if a measurement stop instruction has not been received via the operation portion 52 (step S18: NO), calculation of pulse transit time (step S16) and calculation of blood pressure (step S17) are periodically repeated every time the first pulse wave signal PS1 and the second pulse wave signal PS2 corresponding to the pulse wave are input. The CPU 100 updates and displays the blood pressure value measurement results on the display 50 and cumulatively stores them in the memory 51. Then, if a measurement stop instruction has been received in step S18 (step S18: YES), measurement operation ends.

According to the blood pressure monitor 1, blood pressure can be continuously measured over an extended period of time on the basis of pulse transit time while keeping the physical burden on the user light.

Also, according to the blood pressure monitor 1, blood pressure measurement (estimation) based on pulse transit time and blood pressure measurement via the oscillometric method can be performed by one device. This can increase user convenience.

Figure 9:
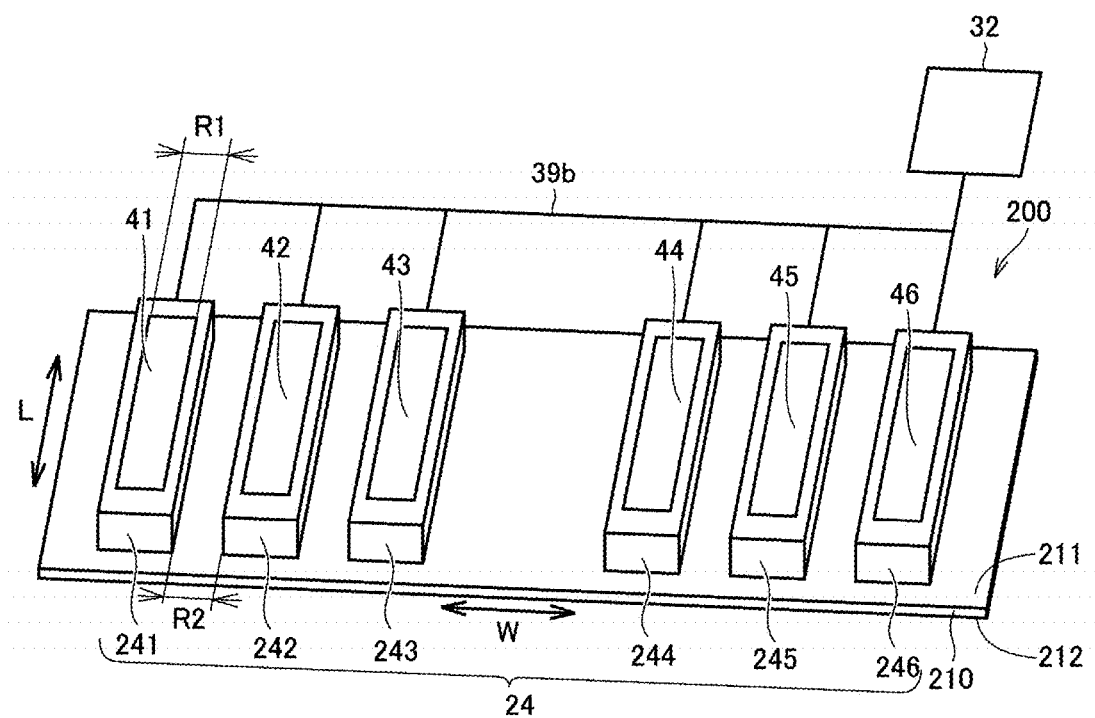
FIG. 9 is a perspective view illustrating the pulse wave measurement electrode unit according to the first embodiment.

FIG. 9 is a perspective view illustrating the pulse wave measurement electrode unit according to the first embodiment. The detailed configuration of the pulse wave measurement electrode unit 200 according to the first embodiment will be described with reference to FIG. 9.

As illustrated in FIG. 9, the pulse wave measurement electrode unit 200 includes the electrodes 41 to 46, the support member 210, and the pressing cuff 24.

The electrodes 41 to 46 come into contact with the body surface of the measurement subject in the measurement. The electrodes 41 to 46 have a plate-like like shape. The electrodes 41 to 46 are arranged side by side in the width direction W of the support member 210 described below. The electrodes 41 to 46 are disposed on the front surface of divided bags 241 to 246 described below. The electrodes 41 to 46 are formed by printing or the like.

Of the electrodes 41 to 46, the electrodes 41 and 46 correspond to a pair of current applying electrodes. Of the electrodes 41 to 46, the electrodes 42 and 43 correspond to a first pair of voltage measuring electrodes. Of the electrodes 41 to 46, the electrodes 44 and 45 correspond to a second pair of voltage measuring electrodes. The first pair of voltage measuring electrodes and the second pair of voltage measuring electrodes are disposed between the pair of current applying electrodes.

The support member 210 has a sheet-like shape. The support member 210 includes a first main surface 211 and a second main surface 212 which are opposite one another in the thickness direction. The first main surface 211 faces the body surface of the measurement subject when the blood pressure monitor 1 (pulse wave measurement electrode unit) is in the attachment state of being attached to the measurement subject. The second main surface 212 is the surface on the opposite side from the first main surface 211 in the thickness direction of the support member 210.

The support member 210 includes a length direction L corresponding to the circumferential direction of the device when attached and the width direction W orthogonal to the length direction L and the thickness direction. The support member 210 includes a resin member with insulating properties, for example. The support member 210 has flexibility. However, the support member 210 preferably does not plastically deform when pressed by the compression cuff 21 or the like.

As described above, the pressing cuff 24 is configured to expand by fluid being supplied and press the electrodes 41 to 46 against the body surface of the measurement subject when expanded to perform measurement.

The pressing cuff 24 is disposed on the first main surface 211. The pressing cuff 24 includes the divided bags 241 to 246. The divided bags 241 to 246 are disposed between the electrodes 41 to 46 and the first main surface 211 of the support member 210. The divided bags 241 to 246 are arranged side by side in the width direction W of the support member 210.

The divided bags 241 to 246 are connected to the pump 32 via the air line 39a. The air line 39a is connected to the pump 32 at one end; and, at the other end, branches out and is connected to the divided bags 241 to 246.

The connection destination of the pump 32 and the valve 33 (see FIG. 4) is switched to the pressing cuff 24 via the switching valve 35 (see FIG. 4), and the pump 32 is driven with the valve 33 closed. This supplies fluid to the divided bags 241 to 246. As a result, the divided bags 241 to 246 expand. When the valve 33 is opened with the pump 32 stopped, the air in the divided bags 241 to 246 is discharged out.

The pulse wave measurement electrode unit 200 is provided with low rigidity portions R2 between adjacent electrodes. The low rigidity portions R2 have a lower rigidity than that of portions R1 that overlap the electrodes in the thickness direction. The low rigidity of the low rigidity portions R2 is due to the formation of gaps between adjacent divided bags.

The divided bags 241 to 246 and the support member 210 are stacked in the thickness direction at the portions R1 overlapping the electrodes 41 to 46 in the thickness direction. Gaps are formed between adjacent divided bags, and only the support member 210 is disposed in these portions. Thus, the portions of the pulse wave measurement electrode unit 200 located between adjacent electrodes have a lower rigidity than that of the portions R1 overlapping the electrodes in the thickness direction.

By disposing the low rigidity portions between adjacent electrodes in this way, the movement of the electrodes 41 to 46 when attaching the pulse wave measurement electrode unit 200 to the measurement subject is improved. Accordingly, the electrodes 41 to 46 can be brought into suitable contact with an uneven body surface. As a result, the precision of detecting biological information can be improved.

Second Embodiment

Figure 10:
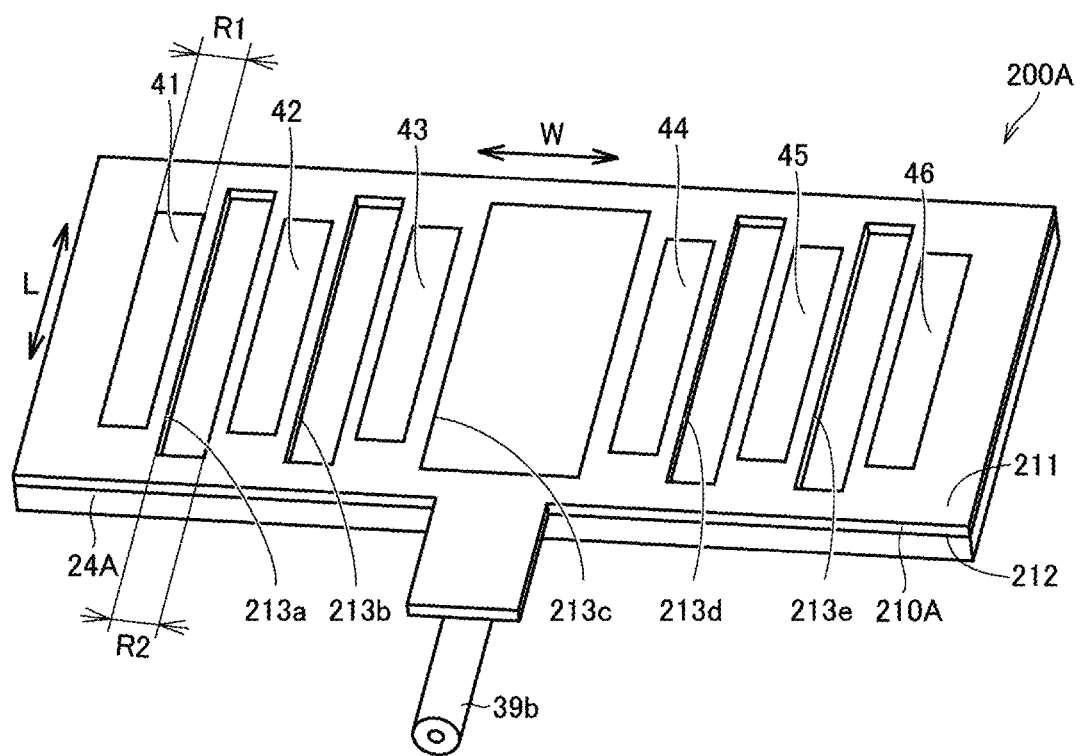
FIG. 10 is a perspective view illustrating a pulse wave measurement electrode unit according to a second embodiment.

FIG. 10 is a perspective view illustrating a pulse wave measurement electrode unit according to a second embodiment. A pulse wave measurement electrode unit 200A according to the second embodiment will be described with reference to FIG. 10.

As illustrated in FIG. 10, the pulse wave measurement electrode unit 200A according to the second embodiment is different from the pulse wave measurement electrode unit 200 of the first embodiment in that a support member 210A and a pressing cuff 24A have a different configuration. Other configurations are substantially similar.

The support member 210A is different from the support member 210 according to the first embodiment in that opening portions 213a to 213e are provided. Other configurations are substantially similar.

The opening portions 213a to 213e are provided between adjacent electrodes. The opening portion 213a is provided between the electrode 41 and the electrode 42. The opening portion 213b is provided between the electrode 42 and the electrode 43. The opening portion 213c is provided between the electrode 43 and the electrode 44. The opening portion 213d is provided between the electrode 44 and the electrode 45. The opening portion 213e is provided between the electrode 45 and the electrode 46.

The electrodes 41 to 46 are provided on the first main surface 211 of the support member 210A. The electrodes 41 to 46 are formed on the first main surface 211 by printing, vapor deposition, photolithography, or other such method.

The pressing cuff 24A is disposed on the second main surface 212 side of the support member 210A. The pressing cuff 24A is disposed overlapping all of the support member 210A when viewed in the direction in which the support member 210A and the pressing cuff 24A overlap. The pressing cuff 24A is exposed from the opening portions 213a to 213e when the pulse wave measurement electrode unit 200 is viewed from the first main surface 211 in the direction in which the support member 210A and the pressing cuff 24A overlap.

The pulse wave measurement electrode unit 200A is provided with low rigidity portions R2 between adjacent electrodes. The low rigidity portions R2 have a lower rigidity than that of portions R1 that overlap the electrodes in the thickness direction. The low rigidity of the low rigidity portions R2 is due to providing the opening portions 213a to 213e in the support member 210A at portions located between adjacent electrodes.

The pressing cuff 24A and the support member 210A are stacked in the thickness direction at the portions R1 overlapping the electrodes 41 to 46 in the thickness direction. The opening portions are formed in the support member 210A between adjacent electrodes, and only the pressing cuff 24A is disposed in these portions. Thus, the portions of the pulse wave measurement electrode unit 200A located between adjacent electrodes have a lower rigidity than that of the portions R1 overlapping the electrodes in the thickness direction.

Also, by providing the opening portions 213a to 213e, compared to a configuration in which the opening portions 213a to 213e are not provided, the rigidity of the support member 210A at the portions around the opening portions 213a to 213e between adjacent electrodes is decreased.

With such a configuration, the pulse wave measurement electrode unit 200A according to the second embodiment can obtain effects similar to that of the pulse wave measurement electrode unit 200 according to the first embodiment.

Third Embodiment

Figure 11:
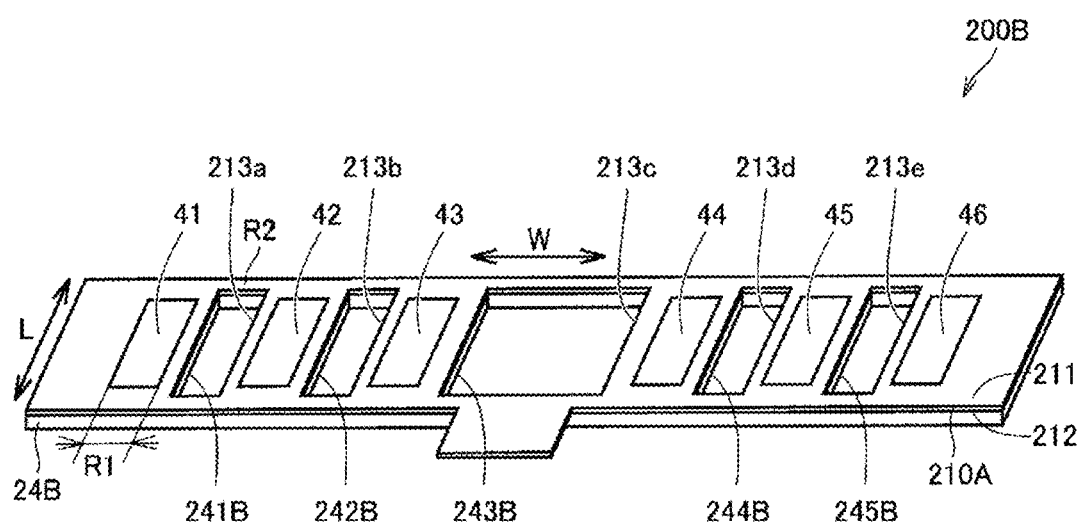
FIG. 11 is a perspective view illustrating a pulse wave measurement electrode unit according to a third embodiment.

FIG. 11 is a perspective view illustrating a pulse wave measurement electrode unit according to a third embodiment. A pulse wave measurement electrode unit 200B according to the third embodiment will be described with reference to FIG. 11.

As illustrated in FIG. 11, the pulse wave measurement electrode unit 200B according to the third embodiment is different from the pulse wave measurement electrode unit 200A of the second embodiment in that a pressing cuff 24B has a different configuration. Other configurations are substantially similar.

The portion of the pressing cuff 24B corresponding to the opening portions 213a to 213e provided on the support member 210A correspond to opening portions 241B to 245B.

In the third embodiment, the portions of the pulse wave measurement electrode unit 200B located near the opening portions 213a to 213e and the opening portions 241B to 245B corresponds to the low rigidity portions R2. The low rigidity of the low rigidity portions R2 is due to providing the opening portions 213a to 213e and the opening portions 241B to 245B.

By providing the opening portions 213a to 213e on the support member 210A, compared to a configuration in which the opening portions 213a to 213e are not provided, the rigidity of the support member 210A at the portions around the opening portions 213a to 213e between adjacent electrodes is decreased.

Also, by providing the opening portions 241B to 245B, compared to a configuration in which the opening portions 241B to 245B are not provided, the rigidity of the pressing cuff 24B at the portions around the opening portions 241B to 245B between adjacent electrodes is decreased.

With such a configuration, the pulse wave measurement electrode unit 200B according to the third embodiment can obtain effects similar to that of the pulse wave measurement electrode unit 200A according to the second embodiment.

Fourth Embodiment

Figure 12:
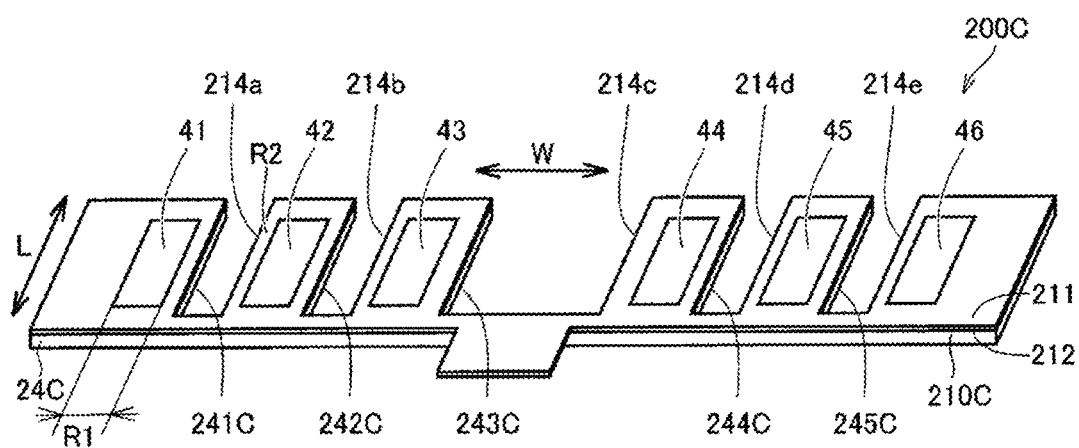
FIG. 12 is a perspective view illustrating a pulse wave measurement electrode unit according to a fourth embodiment.

FIG. 12 is a perspective view illustrating a pulse wave measurement electrode unit according to a fourth embodiment. A pulse wave measurement electrode unit 200C according to the fourth embodiment will be described with reference to FIG. 12.

As illustrated in FIG. 12, the pulse wave measurement electrode unit 200C according to the fourth embodiment is different from the pulse wave measurement electrode unit 200B of the third embodiment in that a support member 210C and a pressing cuff 24C have a different configuration. Other configurations are substantially similar.

The support member 210C is different from the support member 210A according to the third embodiment in that notch portions 214a to 214e are provided instead of the opening portions 213a to 213e. Other configurations are substantially similar.

The notch portions 214a to 214e are provided between adjacent electrodes. The plurality of notch portions 214a to 214e are provided opening to one end in the length direction L of the support member 210C.

Note that the notch portions 214a to 214e may be provided opening to the other end in the length direction L of the support member 210C, or may be provided alternately opening to one end and then the other end in the length direction L of the support member 210C.

The portion of the pressing cuff 24B corresponding to the notch portions 214a to 214e provided on the support member 210C correspond to notch portions 241C to 245C.

In the fourth embodiment, the portions of the pulse wave measurement electrode unit 200C located near the notch portions 214a to 214e and the notch portions 241C to 245C corresponds to the low rigidity portions R2. The low rigidity of the low rigidity portions R2 is due to providing the notch portions 214a to 214e and the notch portions 241C to 245C.

By providing the notch portions 214a to 214e on the support member 210C, compared to a configuration in which the notch portions 214a to 214e are not provided, the rigidity of the support member 210C at the portions around the notch portions 214a to 214e between adjacent electrodes is decreased.

Also, by providing the notch portions 241C to 245C, compared to a configuration in which the notch portions 241C to 245C are not provided, the rigidity of the pressing cuff 24C at the portions around the notch portions 241C to 245C between adjacent electrodes is decreased.

With such a configuration, the pulse wave measurement electrode unit 200C according to the fourth embodiment can obtain effects similar to that of the pulse wave measurement electrode unit 200B according to the third embodiment.

Note that in the fourth embodiment, the notch portions 241C to 245C are provided in the pressing cuff 24C. However, no such limitation is intended, and the notch portions 241C to 245C may not be provided. In this case, the low rigidity of the low rigidity portions R2 provided between adjacent electrodes is due to providing the notch portions 214a to 214e in the support member 210C at portions located between adjacent electrodes.

The configuration given as an example of the embodiment described above is an example configuration of the present disclosure. The configuration can be combined with other known technology, and parts thereof may be omitted or modified within the scope of the present disclosure.

In the first to fourth embodiments described above, the pulse wave measurement electrode unit is provided in a wrist blood pressure monitor configured to be attached on the wrist of the measurement subject. However, no such limitation is intended. For example, it may be provided in a blood pressure monitor attached to a site other than the wrist. The pulse wave measurement electrode unit may be provided in the belt 20 of the blood pressure monitor 1 without the compression cuff 21. In this case, the pulse wave measurement device does not have a blood pressure measurement function and functions as a blood pressure estimation device that estimates the blood pressure from detected pulse wave information.

In the second to fourth embodiments, the pressing cuff of the pulse wave measurement electrode unit is provided independently of the compression cuff of the blood pressure monitor 1. However, no such limitation is intended, and the pressing cuff and the compression cuff may be configured as a single cuff, and the pressing cuff may be a part of the compression cuff. In this case, the compression cuff functions as a fluid bag.

The embodiments described herein are illustrative in all respects and are not intended as limitations. The scope of the present disclosure is indicated by the claims and includes all meaning equivalent to the scope and changes within the scope.

REFERENCE SIGNS LIST

1 Blood pressure monitor
10 Body
10b Bottom surface
15 Buckle
20 Belt
20a Inner circumferential surface
20b Outer circumferential surface
20e, 20f End portion
21 Compression cuff
21a Inner circumferential surface
23 Band
23a Inner circumferential surface
24, 24A, 24B, 24C Pressing cuff
25 First plate-like member
25e, 25f End portion
26 Second plate-like member
26e, 26f End portion
27, 28 Connecting rod
29 Fixing portion
31 First pressure sensor
32 Pump
33 Valve
34 Second pressure sensor
35 Switching valve
38a, 38b, 39a, 39b Air line
40 Impedance measurement portion
40E Electrode group
41, 42, 43, 44, 45, 46 Electrode
49 Current flow and voltage detection circuit
50 Display
51 Memory
52 Operation portion
53 Battery
59 Communication unit
71, 72 Wire
90 Left wrist
90a Palm side surface
91 Radial artery
200, 200A, 200B, 200C Pulse wave measurement electrode unit
210, 210A, 210C Support member
211 First main surface
212 Second main surface
213a, 213b, 213c, 213d, 213e Opening portion
214a, 214e, 241, 242, 243, 245, 246 Divided bag
241B, 242B, 243B, 244B, 245B Opening portion
241C, 242C, 243C, 244C, 245C Notch portion
310, 340 Oscillation circuit
320 Pump drive circuit
401 First pulse wave sensor
402 Second pulse wave sensor
900 Network

The invention claimed is:

1. A pulse wave measurement electrode unit configured to be attached wrapped around a measurement subject for pulse wave measurement of a measurement subject, comprising:
   electrodes comprising a pair of current applying electrodes and a first pair of voltage measuring electrodes, the electrodes coming into contact with a body surface of the measurement subject for measurement;
   a support member comprising a first main surface that faces the body surface of the measurement subject in a case that the pulse wave measurement electrode unit is attached to the measurement subject and a second main surface, which is a surface opposite the first main surface in a thickness direction, the support member supporting the electrodes on the first main surface; and
   a fluid bag configured to expand and contract via the supply and discharge of fluid and configured to expand upon measurement to press the electrodes against the body surface of the measurement subject; wherein
   the support member comprises a length direction corresponding to a circumferential direction of the pulse wave measurement electrode unit in an attached state to the measurement subject and a width direction orthogonal to the length direction and the thickness direction;
   the electrodes are arranged side by side in the width direction;
   low rigidity portions are provided between adjacent electrodes of the electrodes, the low rigidity portions having a lower rigidity than a rigidity of portions overlapping the electrodes in the thickness direction;
   the fluid bag comprises divided bags separated from one another in the width direction and disposed between the electrodes and the first main surface of the support member; and
   the low rigidity portions have a low rigidity due to gaps being provided between adjacent divided bags of the divided bags.

2. A pulse wave measurement electrode unit configured to be attached wrapped around a measurement subject for pulse wave measurement of a measurement subject, comprising:
   electrodes comprising a pair of current applying electrodes and a first pair of voltage measuring electrodes, the electrodes coming into contact with a body surface of the measurement subject for measurement;
   a support member comprising a first main surface that faces the body surface of the measurement subject in a case that the pulse wave measurement electrode unit is attached to the measurement subject and a second main surface, which is a surface opposite the first main surface in a thickness direction, the support member supporting the electrodes on the first main surface; and
   a fluid bag configured to expand and contract via the supply and discharge of fluid and configured to expand upon measurement to press the electrodes against the body surface of the measurement subject; wherein
   the support member comprises a length direction corresponding to a circumferential direction of the pulse wave measurement electrode unit in an attached state to the measurement subject and a width direction orthogonal to the length direction and the thickness direction;
   the electrodes are arranged side by side in the width direction;
   low rigidity portions are provided between adjacent electrodes of the electrodes, the low rigidity portions having a lower rigidity than a rigidity of portions overlapping the electrodes in the thickness direction;

the electrodes are provided on the first main surface;

the fluid bag is disposed on the second main surface;

the low rigidity portions have a low rigidity due to notch portions or opening portions being provided in the support member at portions located between the adjacent electrodes; and the fluid bag comprises notch portions or opening portions at portions corresponding to the notch portions or the opening portions of the support member.

3. The pulse wave measurement electrode unit according to claim 1, wherein the electrodes comprise a second pair of voltage measuring electrodes; and the first pair of voltage measuring electrodes and the second pair of voltage measuring electrodes are disposed between the pair of current applying electrodes.

4. A pulse wave measurement device, comprising:

the pulse wave measurement electrode unit according to claim 1; and a belt member configured to support the pulse wave measurement electrode unit and wrap around a measurement site of a measurement subject.

5. The pulse wave measurement electrode unit according to claim 2, wherein the electrodes comprise a second pair of voltage measuring electrodes; and the first pair of voltage measuring electrodes and the second pair of voltage measuring electrodes are disposed between the pair of current applying electrodes.

6. A pulse wave measurement device, comprising:

the pulse wave measurement electrode unit according to claim 2; and a belt member configured to support the pulse wave measurement electrode unit and wrap around a measurement site of a measurement subject.

* * * * *